United States Patent [19]
Nakamura et al.

[11] Patent Number: 5,808,149
[45] Date of Patent: Sep. 15, 1998

[54] METHOD FOR PRODUCING HIGH-PURITY FLUOROALKYLSULFONIC ACID ANHYDRIDE

[75] Inventors: Tamio Nakamura; Masahiro Tainaka; Yasushi Kita; Shoji Okabayashi; Seigo Okamura, all of Ube, Japan

[73] Assignee: Central Glass Company, Limited, Yamaguchi, Japan

[21] Appl. No.: 771,118

[22] Filed: Dec. 20, 1996

[30] Foreign Application Priority Data

Dec. 20, 1995 [JP] Japan .................................. 7-331932
Jan. 23, 1996 [JP] Japan .................................. 8-008783

[51] Int. Cl.$^6$ ...................................................... C07F 9/02
[52] U.S. Cl. .............................................................. 562/872
[58] Field of Search ............................................... 562/872

[56] References Cited

U.S. PATENT DOCUMENTS 5,004,829  4/1991  Aramaki et al. ........................ 562/872

*Primary Examiner*—Paul J. Killos
*Attorney, Agent, or Firm*—Evenson, McKeown, Edwards & Lenahan, P.L.L.C.

[57] ABSTRACT

The present invention relates to a method for producing a fluoroalkylsulfonic acid anhydride represented by a general formula of $(C_nF_{2n+1}SO_2)_2O$ where n is an integer ranging from 1 to 8. This method includes a step of (a) reacting diphosphorus pentoxide with a fluoroalkylsulfonic acid represented by a general formula of $C_nF_{2n+1}SO_3H$ where n is an integer ranging from 1 to 8, in a fluorine-containing solvent, thereby to form the fluoroalkylsulfonic acid anhydride in the fluorine-containing solvent. A fluoroalkylsulfonic acid anhydride produced by this method is high in purity and yield.

39 Claims, No Drawings

METHOD FOR PRODUCING HIGH-PURITY FLUOROALKYLSULFONIC ACID ANHYDRIDE

BACKGROUND OF THE INVENTION

This invention relates to methods for producing fluoroalkylsulfonic acid anhydrides which are useful, for example, as catalyst for synthesis of medicines, organic compounds and the like and as light-generating acid catalyst of chemical-amplification-type resist.

There is a conventional method for producing fluoroalkylsulfonic acid anhydrides represented by the general formula of $(C_nF_{2n+1}SO_2)_2O$. In this method, for example, trifluoromethanesulfonic acid anhydride is produced by adding diphosphorus pentoxide to trifluoromethanesulfonic acid to allow the reaction therebetween, as shown by the following reaction formula (1), followed by distillation. With this, crude trifluoromethanesulfonic acid anhydride is obtained. Then, this crude product is rectified to obtain pure trifluoromethanesulfonic acid anhydride.

$$6\ CF_3SO_3H + P_2O_5 \rightarrow 3(CF_3SO_2)_2O + 2H_3PO_4 \qquad (1)$$

The reaction of the above method is a dehydrocondensation reaction (i.e., condensation reaction with elimination of water) of trifluoromethanesulfonic acid. In this method, diphosphorus pentoxide is added to trifluoromethanesulfonic acid. Therefore, if diphosphorus pentoxide is added in an excessive amount that is not less than 5 moles per 6 moles of trifluoromethanesulfonic acid, the reaction liquid solidifies. After this solidification, the reaction does not proceed further, even if diphosphorus pentoxide is added further. Thus, conversion of trifluoromethanesulfonic acid does not exceed an upper limit of about 70%, and about 30% of trifluoromethanesulfonic acid remains unreacted. A Furthermore, even after the distillation, some of the trifluoromethanesulfonic acid anhydride remains unrecovered in the distillation residue, depending on the distillation conditions, such as pressure and temperature. Due to this, yield of trifluoromethanesulfonic acid becomes as low as about 60%. In view of this, there is a proposal to recover the unreacted trifluoromethanesulfonic acid by adding water or phosphoric acid aqueous solution to the distillation residue that remains after the recovery of trifluoromethanesulfonic acid anhydride by distillation (see Japanese Patent Unexamined Publication JP-A-Hei-2-268148). When the reaction mixture is maintained to allow diphosphorus pentoxide to react with the fluoroalkylsulfonic acid, followed by heating during the distillation, the obtained is trifluoromethanesulfonic acid anhydride may be decomposed by the unreacted trifluoromethanesulfonic acid, as shown in the following reaction formula (2).

$$(CF_3SO_2)_2O \rightarrow CF_3SO_2.OCF_3 \uparrow + SO_2 \uparrow \qquad (2)$$

Thus, the trifluoromethanesulfonic acid anhydride recovered by distillation may be contaminated with large amounts of trifluoromethanesulfonic acid ester and trifluoromethanesulfonic acid. These impurities can almost completely be eliminated by rectification. However, the separation efficiency in the rectification is inferior.

SUMMARY OF THE INVENTION

It is an object of the present invention to provide a method for producing a fluoroalkylsulfonic acid anhydride that is low in impurities concentration and high in yield.

It is another object of the present invention to provide a method for producing a trifluoromethanesulfonic acid anhydride that is low in impurities concentration and high in yield.

According to the present invention, there is provided a first method for producing a fluoroalkylsulfonic acid anhydride represented by a general formula of $(C_nF_{2n+1}SO_2)_2O$ where n is an integer ranging from 1 to 8. The first method comprises a step of (a) reacting diphosphorus pentoxide with a fluoroalkylsulfonic acid represented by a general formula of $C_nF_{2n+1}SO_3H$ where n is an integer ranging from 1 to 8, in a fluorine-containing solvent, thereby to form the fluoroalkylsulfonic acid anhydride in the fluorine-containing solvent. In the invention, the fluoroalkylsulfonic acid used in the step (a) is, for example, trifluoromethanesulfonic acid. In this case, the reaction product, the fluoroalkylsulfonic acid anhydride, becomes trifluoromethanesulfonic acid anhydride. According to the present invention, the fluoroalkylsulfonic acid anhydride (e.g., trifluoromethanesulfonic acid anhydride) obtained by the step (a) may be recovered by a second method comprising steps of:

(b) recovering the fluoroalkylsulfonic acid anhydride from a first reaction mixture formed by the step (a), for example, by distillation, thereby to leave a residue;

(c) adding phosphoric acid to the residue, thereby to prepare a second reaction mixture; and (d) further recovering the fluoroalkylsulfonic acid anhydride from the residue contained in the second reaction mixture, by distillation.

Due to the provision of the steps (c) and (d) in addition to the step (b), it becomes possible to obtain fluoroalkylsulfonic acid anhydride that is very high in purity and yield. In the step (c), it is preferable to use phosphoric acid containing free water as little as possible. With this, the recovery of the fluoroalkylsulfonic acid anhydride in the step (d) becomes very high.

According to the present invention, the step (a) of the first method may be conducted by the following subordinate steps of:

(1) adding diphosphorus pentoxide to a fluorine-containing solvent, thereby to prepare a slurry;

(2) adding the fluoroalkylsulfonic acid to the slurry, thereby to prepare a reaction mixture; and (3) maintaining the reaction mixture at a temperature of from −40° to 150° C., thereby to allow the diphosphorus pentoxide to react with the fluoroalkylsulfonic acid in the fluorine-containing solvent.

According to the subordinate steps of (1), (2) and (3), conversion of the fluoroalkylsulfonic acid becomes almost 100%, under the following first and second preferable is conditions, thereby to obtain the fluoroalkylsulfonic acid anhydride which is substantially low in impurities concentration. As the first condition, the diphosphorus pentoxide is preferably in an amount far more than the stoichiometric amount (i.e., 1 mol per 6 moles of the fluoroalkylsulfonic acid, as shown in the reaction formula (1)). In other words, the amount of diphosphorus pentoxide is preferably from 2 to 66.7 moles per 6 moles of the fluoroalkylsulfonic acid. Furthermore, when trifluoromethanesulfonic acid is used as the fluoroalkylsulfonic acid, the amount of diphosphorus pentoxide is preferably from 2 to 20 moles per 6 moles of trifluoromethanesulfonic acid. As the second condition, the reaction between diphosphorus pentoxide and the fluoroalkylsulfonic acid is conducted at a relatively low temperature of from −40° to 150° C., preferably from 0° to 10° C. The above first condition can be achieved by using a fluorine-containing solvent of the present invention for dispersing therein diphosphorus pentoxide. Under the above first and second conditions, the reaction mixture in the form of slurry does not solidify. With this, a sufficient reaction time can be taken, thereby to make the conversion of fluoroalkylsulfonic acid almost 100%, as mentioned above.

As an alternative to the above subordinate steps of (1), (2) and (3), the step (a) of the first method may be conducted by the following subordinate steps of:

(1') adding the fluoroalkylsulfonic acid to the fluorine-containing solvent, thereby to prepare a solution;

(2') adding diphosphorus pentoxide to the solution, thereby to prepare a reaction mixture; and (3') maintaining the reaction mixture at a temperature of from −40° to 150° C., thereby to allow the diphosphorus pentoxide to react with the fluoroalkylsulfonic acid in the fluorine-containing solvent.

According to the subordinate steps of (1'), (2') and (3'), conversion of the fluoroalkylsulfonic acid becomes at least 90%, under a preferable condition in which diphosphorus pentoxide is intermittently added in parts to the solution in the step (2'). Under this condition, a larger amount of diphosphorus pentoxide is reacted with fluoroalkylsulfonic acid, as compared with a condition in which the total amount of diphosphorus pentoxide is added thereto at one time. Furthermore, under this condition, the reaction mixture in the form of slurry does not solidify, even at room temperature. With this, a sufficient reaction time can be taken, thereby to make the conversion of fluoroalkylsulfonic acid at least 90%, as mentioned above.

In the invention, the fluoroalkylsulfonic acid anhydride, which is the reaction product itself of the step (a) of the first method, is preferably used as a fluorine-containing solvent of the step (a). With this, the recovered reaction product is not contaminated at all with the solvent, thereby to obtain the fluoroalkylsulfonic acid anhydride that is very low in impurities concentration.

DESCRIPTION OF THE PREFERRED EMBODIMENTS

In the following, a method for producing a fluoroalkylsulfonic acid anhydride will be described in detail in accordance with the present invention.

In the step (a) of the first method, diphosphorus pentoxide is in an amount preferably not greater than 80 wt %, more preferably of from 15–30 wt %, based on the total weight of the diphosphorus pentoxide and the fluorine-containing solvent. Its amount is preferably not less than 5 wt %, from the economical reason. If its amount is greater than 80 wt %, the reaction mixture (slurry) may solidify within a short period of time. With this, it may become impossible to take a sufficient time for conducting the solid-liquid reaction of the step (a), and thus conversion of fluoroalkylsulfonic acid may become too low.

In the subordinate steps (1), (2) and (3), diphosphorus pentoxide is in an amount preferably from 2 to 66.7 moles, more preferably from 8 to 40 moles, per 6 moles of the fluoroalkylsulfonic acid. If it is less than 2 moles, the reaction rate way become too slow, and the formation of fluoroalkylsulfonic acid ester may be accelerated. With this, yield may become too low. More than 66.7 moles does not bring a particular disadvantage, but is uneconomical. In case that trifluoromethanesulfonic acid is used, diphosphorus pentoxide is in an amount preferably from 2 to 20 moles, more preferably from 8 to 10 moles, per 6 moles of the fluoroalkylsulfonic acid. In the subordinate steps (1'), (2') and (3'), diphosphorus pentoxide is in an amount preferably from 2 to 100 moles, more preferably from 4 to 10 moles, per 6 moles of the fluoroalkylsulfonic acid. The above descriptions for the case of being outside of the range (2–66.7 moles) also respectively apply in the cases of being outside of the range (2–20 moles) and the range (2–100 moles).

In the subordinate step (1'), the fluoroalkylsulfonic acid is in an amount preferably not greater than 50 wt %, more preferably from 20 to 30 wt %, based on the total weight of the fluoroalkylsulfonic acid and the fluorine-containing solvent. Its amount is preferably not less than 5 wt %, from the economical reason. If it is greater than 50 wt % in case that the fluoroalkylsulfonic acid anhydride is used as the fluorine containing solvent, esterification of the fluoroalkylsulfonic acid anhydride by the fluoroalkylsulfonic acid may be accelerated, thereby to lower yield of the fluoroalkylsulfonic acid anhydride. In the above case, this esterification occurs at room temperature or higher temperature. Therefore, in the above case, it is preferable to add diphosphorus pentoxide as soon as possible, after the addition of the fluoroalkylsulfonic acid to the fluoroalkylsulfonic acid anhydride used as the fluorine-containing solvent.

In the subordinate step (2'), it is preferable that diphosphorus pentoxide is intermittently added in parts, while the reaction mixture is stirred. For example, in case that diphosphorus pentoxide is added in total in an amount of 5 moles per 6 moles of the fluoroalkylsulfonic acid, and that the reaction temperature of the step (3') is 30° C., it is preferable that the total amount of diphosphorus pentoxide is separated into five portions, and each portion is added at an interval of at least three hours. If each portion is added at an interval of less than three hours, the reaction mixture (slurry) may somewhat solidify, thereby to lower conversion of the fluoroalkylsulfonic acid As an alternative to the intermittent addition, it is optional to gradually continuously add the total amount of diphosphorus pentoxide in the step (2').

In each of the subordinate steps (3) and (3') of the step (a), the reaction mixture is maintained at a temperature preferably from −40° to 150° C. It is more preferably from 0° to 10° C. and from 20° to 40° C. in the steps (3) and (3'), respectively. If it is higher than 150° C. in the steps (3) and (3'), the reaction mixture (slurry) may solidify within a short period of time. With this, it may become impossible to take a sufficient time for conducting the solid-liquid reaction of the step (a), and thus conversion of fluoroalkylsulfonic acid may become too low. If it is lower than −40° C. in the steps (3) and (3'), the reaction rate may become too slow, and the reaction mixture may become too high in viscosity. In case that trifluoromethanesulfonic acid is used, the reaction mixture is maintained at a temperature preferably from −40° to 100° C., is more preferably from 0° to 10° C. The above descriptions for the case of being outside of the range (−40°–150° C.) also apply in the case of being outside of the range (0°–10° C.).

In the step (3), it is preferable to conduct the reaction at a temperature from 0° to 10° C. for at least 30 minutes, more preferably from 8 to 10 hr, while the reaction mixture is stirred under atmospheric pressure or reduced pressure. In the step (3'), it is preferable to conduct the reaction at a temperature from 20° to 40° C. for at least 30 minutes, more preferably from 15 to 30 hr, while the reaction mixture is stirred under atmospheric pressure or reduced pressure Examples of the fluorine-containing solvent used in the step (a) are fluoroalkylsulfonic acid anhydrides each represented by a general formula of $(C_nF_{2n+1}SO_2)_2O$ where n is an integer ranging from 1 to 8, fluoroalkylsulfonic acid esters each represented by a general formula of $C_nF_{2n+1}SO_2.OC_nF_{2n+1}$ where n is an integer ranging from 1 to 8, such as trifluoromethyltrifluoromethanesulfonic acid ester represented by a formula of $CF_3SO_2.OCF_3$, perfluoroalkanes each represented by a general formula of $C_nF_{2n+2}$ where n is an integer ranging from 4 to 20, perfluoroalkylamines each represented by a general formula of $(C_nF_{2n+1})_3N$ where n is an integer ranging from 2 to 6, perfluoro compounds such as perfluoro polyethers, and mixtures of at least two of these. Of these, the fluoroalkylsulfonic acid anhydride is the most preferably used as the solvent. Even if a fluorine-containing solvent other than the fluoroalkylsulfonic acid anhydride is used, it is possible to produce the fluoroalkylsulfonic acid anhydride of high purity by conducting the steps (a)–(d).

In the step (c) of the second method for recovering the fluoroalkylsulfonic acid anhydride, it is preferable to use phosphoric acid containing free water as little as possible in order to suppress hydrolysis of the fluoroalkylsulfonic acid is anhydride remaining in the second reaction mixture of the step (c). Furthermore, it is preferable to use phosphoric acid of 100%, which contains 72.4% of $P_2O_5$, or of more than 100%. The $P_2O_5$ concentration of the phosphoric acid does not have a particular upper limit. However, if it is too high, the amount of the residue, which remains after the step (d) and is mainly made of diphosphorus pentoxide, may increase too much. Thus, it may become cumbersome to treat the reaction residue. The $P_2O_5$ concentration of the phosphoric acid is preferably not higher than 80% under normal conditions.

In the step (c), phosphoric acid is preferably in an amount such that the total of this phosphoric acid and the residue of the step (c) contains up to 2 moles of bound water, per mol of the total, on the basis of $P_2O_5$, of the phosphoric acid and the diphosphorus pentoxide contained in the residue of the step (c). This bound water is a contrast to free water causing hydrolysis of the fluoroalkylsulfonic acid anhydride. By adding the above amount of phosphoric acid to the residue in the step (c), the total of the phosphoric acid and the diphosphorus pentoxide will have a composition of pyrophosphoric acid In other words, after the step (d) in which the fluoroalkylsulfonic acid anhydride is further recovered, the residue becomes a pyrophosphoric acid solution. If too much amount of phosphoric acid is added in the step (c), too much amount of free water may be formed, thereby to cause hydrolysis of the fluoroalkylsulfonic acid anhydride contained in the residue of the step (c). With this, the recovery of the fluoroalkylsulfonic acid anhydride in the step (d) may become too low. Strictly speaking, it is preferable to decide the amount of phosphoric acid used in the step (c), in consideration of the amount of water formed by dehydrocondensation of the fluoroalkylsulfonic acid.

The second reaction mixture (phosphoric acid solution) of the step (c) prepared by adding phosphoric acid in a suitable amount as mentioned above has a characteristic that the fluoroalkylsulfonic acid anhydride hardly dissolves therein, but the fluoroalkylsulfonic acid dissolves infinitely therein. Due to this characteristic, distillation of the step (d) can be conducted at a low temperature, thereby to obtain the fluoroalkylsulfonic acid anhydride of high purity.

It is optional to add a suitable amount of water to the residue remaining after the step (d) in another reaction vessel which is different from that for the steps (a) to (d) so as to prepare a 100% phosphoric acid solution, which is reusable in the step (c).

The fluoroalkylsulfonic acid used as a raw material of the first method may contain certain amounts of impurities such as sulfur trioxide, sulfuric acid and water. At room temperature or higher temperature, these impurities may cause diphosphorus pentoxide, the fluoroalkylsulfonic acid, and the fluoroalkylsulfonic acid anhydride to decompose, as shown in the following reaction formulas (3)–(5). The decomposition of these compounds is accelerated under the heated condition during the distillation. Therefore, the concentration of these impurities in the fluoroalkylsulfonic acid is preferably up to 1,000 ppm, more preferably up to 500 ppm.

$$H_2SO_4 + P_2O_5 \rightarrow SO_3 + 2HPO_3 \qquad (3)$$

$$2C_nF_{2n+1}SO_3H + SO_3 \rightarrow C_nF_{2n+1}SO_2.OC_nF_{2n+1} + SO_2\uparrow + H_2SO_4 \qquad (4)$$

$$(C_nF_{2n+1}SO_2)_2O + H_2O \uparrow 2C_nF_{2n+1}SO_3H \qquad (5)$$

In the step (b), the fluoroalkylsulfonic acid anhydride is recovered by solvent extraction, distillation or the like. Of these, distillation is preferably used For example, in case of trifluoromethanesulfonic acid anhydride, it is distilled off from the first reaction mixture under a pressure preferably of at least 50 torr, more preferably of at least 100 torr. If the is pressure is too high, trifluoromethanesulfonic acid anhydride may be pyrolyzed, thereby to increase the production of free fluorine. Thus, the distillation pressure is preferably from about 150 to about 200 torr.

In the invention, it is preferable to use reaction vessel and distillation still which are made of stainless steel, Hastelloy-C, or the like, and to use distilling column, condenser, and the reaction product's receiver which are made of glass, a material lined with glass or TEFLON (trade name), or the like.

The following nonlimitative Examples 1–21 are illustrative of the present invention.

EXAMPLE 1

In this example, trifluoromethanesulfonic acid anhydride was produced in accordance with the present invention, as follows.

At first, a reactor that is equipped with a jacket, a coil and a stirrer and has a capacity of $0.27 \text{ m}^3$ was charged with 320 kg of a trifluoromethanesulfonic acid anhydride (fluorine-containing solvent) that has a purity of at least 99 wt % and contains up to 0.5 wt % of trifluoromethanesulfonic acid ester, up to 0.5 wt % of trifluoromethanesulfonic acid, up to 5 wt ppm of phosphorus, and 100 wt ppm of free fluorine. Then, 80 kg (10 moles per 6 moles of trifluoromethanesulfonic acid) of diphosphorus pentoxide was added to the solvent, while the solvent was maintained at 5° C., by allowing cold water to flow through the coil, with stirring. Then, to this slurry containing 20 wt % of diphosphorus pentoxide 50 kg of trifluoromethanesulfonic acid was added. Then, this reaction mixture was maintained at 10° C. for 8 hr with sufficient stirring to conduct the reaction. In this reaction, conversion of trifluoromethanesulfonic acid was 99.5%.

Then, trifluoromethanesulfonic acid anhydride was distilled off by simple distillation from the reaction mixture under a pressure of 160 torr by raising the temperature from 45° C. to 160° C. with the heat medium flow through the jacket. This distillation was continued until the end of boiling of trifluoromethanesulfonic acid anhydride, thereby to obtain 358.1 kg of trifluoromethanesulfonic acid anhydride which is colorless and transparent. By chemical analysis, this first distillate was found to have a purity of at least 99 wt % and contain up to 0.5 wt % of trifluoromethanesulfonic acid ester, up to 0.5 wt % of trifluoromethanesulfonic acid, up to 5 wt ppm of phosphorus, and 500 wt ppm of free fluorine. The actual amount of trifluoromethanesulfonic acid anhydride produced by the reaction was 38.1 kg obtained by subtracting 320 kg from 358.1 kg, and the yield was 81%, based on the amount of trifluoromethanesulfonic acid.

Then, 188 kg of 100% phosphoric acid was added to the residue of the above simple distillation. Then, trifluoromethanesulfonic acid anhydride was again distilled off by simple distillation from the reaction mixture under a pressure of 160 torr by raising the temperature from 45° C. to 90° C. With this, there was obtained 2.4 kg of trifluoromethanesulfonic acid anhydride which is colorless and transparent. By chemical analysis, this second distillate was found to have the same purity and the same impurity concentrations as those of the first distillate. The yield was 5%, based on the amount of trifluoromethanesulfonic acid. Thus, the total yield was 86%.

The residue remaining after the second distillation was polyphosphoric acid in the form of liquid at 90° C., and thus it was possible to easily purge this residue from the reactor.

Separately, 360.5 kg of the obtained crude trifluoromethanesulfonic acid anhydride was rectified under a pressure of 160 torr at 45° C., in order to reduce the free fluorine concentration thereof. In this rectification, refluxing was conducted for 1 hr. After cutting out 18 kg of the initial distillate, the middle distillate was taken out, thereby to obtain 252 kg of a rectified product which is colorless and transparent. By chemical analysis, this rectified product was found to have a purity of at least 99 wt % and contain up to 0.5 wt % of trifluoromethanesulfonic acid ester, up to 0.5 wt % of trifluoromethanesulfonic acid, up to 5 wt ppm of phosphorus, and 30 wt ppm of free fluorine. The initial distillate of the rectification and the crude trifluoromethanesulfonic acid anhydride of the remaining liquid in the reactor were usable as the fluorine-containing solvent.

EXAMPLE 2

In this example, Example 1 was modified as follows. At first, a reactor that is the same as that of Example 1 was charged with 128 kg of a trifluoromethanesulfonic acid anhydride that is the same as that of Example 1. Then, 32 kg 4 moles per 6 moles of trifluoromethanesulfonic acid) of diphosphorus pentoxide was added to the solvent in the same manner as that of Example 1. Then, to this slurry containing 20 wt % of diphosphorus pentoxide 50 kg of trifluoromethanesulfonic acid was added. Then, this reaction mixture was maintained at 10° C. for 16 hr with sufficient stirring to conduct the reaction. In this reaction, conversion of trifluoromethanesulfonic acid was 92%.

Then, the first distillation of Example 1 was repeated, thereby to obtain 164.7 kg of trifluoromethanesulfonic acid anhydride which is colorless and transparent. By chemical analysis, this first distillate was found to have a purity of 98 wt % and contain 1.0 wt % of trifluoromethanesulfonic acid ester, 1.0 wt % of trifluoromethanesulfonic acid, up to 5 wt ppm of phosphorus, and 620 wt ppm of free fluorine. The actual amount of trifluoromethanesulfonic acid anhydride produced by the reaction was 33.4 kg, and the yield was 71%, based on the amount of trifluoromethanesulfonic acid.

Then, 58 kg of 100% phosphoric acid was added to the residue of the first distillation. Then, the second distillation of Example 1 was repeated, thereby to obtain 1.9 kg of trifluoromethanesulfonic acid anhydride which is colorless and transparent. By chemical analysis, this second distillate was found to have a purity of at least 99% and contain up to 0.5 wt % of trifluoromethanesulfonic acid ester, up to 0.5 wt % of trifluoromethanesulfonic acid, up to 5 wt ppm of phosphorus, and 530 wt ppm of free fluorine. The yield was 4%, based on the amount of trifluoromethanesulfonic acid. Thus, the total yield was 75%.

EXAMPLE 3

In this example, Example 1 was modified as follows. At first, a reaction mixture was prepared in the same manner as that of Example 1, by adding trifluoromethanesulfonic acid to the diphosphorus pentoxide slurry. Then, this reaction mixture was maintained at 95° C. to conduct the reaction. 4 hr after the start of the reaction, the reaction mixture (slurry) solidified. Therefore, the reaction was terminated. In this reaction, conversion of trifluoromethanesulfonic acid was 95%.

Then, the first distillation of Example 1 was repeated, thereby to obtain 355.3 kg of trifluoromethanesulfonic acid anhydride which is colorless and transparent. By chemical analysis, this first distillate was found to have a purity of at least 99wt % and contain up to 0.5 wt % of trifluoromethanesulfonic acid ester, up to 0.5 wt % of trifluoromethanesulfonic acid, up to 5 wt ppm of phosphorus, and 550 wt ppm of free fluorine. The actual amount of trifluoromethanesulfonic acid anhydride produced by the reaction was 35.3 kg, and the yield was 75%, based on the amount of trifluoromethanesulfonic acid.

Then, 190 kg of 100% phosphoric acid was added to the residue of the first distillation. Then, the second distillation of Example 1 was repeated, thereby to obtain 2.8 kg of trifluoromethanesulfonic acid anhydride which is colorless and transparent. By chemical analysis, this second distillate was found to have a purity of at least 99% and contain up to 0.5 wt % of trifluoromethanesulfonic acid ester, up to 0.5 wt % of trifluoromethanesulfonic acid, up to 5 wt ppm of phosphorus, and 530 wt ppm of free fluorine. The yield was 6%, based on the amount of trifluoromethanesulfonic acid. Thus, the total yield was 81%.

EXAMPLE 4

In this example, Example 1 was modified as follows. At first, a reactor that is the same as that of Example 1 was charged with 80 kg of a trifluoromethanesulfonic acid anhydride that is the same as that of Example 1. Then, 80 kg (10 moles per 6 moles of trifluoromethanesulfonic acid) of diphosphorus pentoxide was added to the solvent in the same manner as that of Example 1. Then, to this slurry containing 50 wt % of diphosphorus pentoxide 50 kg of trifluoromethanesulfonic acid was added. Then, this reaction mixture was maintained at 10° C. to conduct the reaction. After a lapse of 3 hr, the reaction mixture (slurry) solidified. Therefore, the reaction was terminated. In this reaction, conversion of trifluoromethanesulfonic acid was 94%.

Then, the first distillation of Example 1 was repeated, thereby to obtain 114.3 kg of trifluoromethanesulfonic acid anhydride which is colorless and transparent. By chemical analysis, this first distillate was found to have a purity of at least 99 wt % and contain up to 0.5 wt % of trifluoromethanesulfonic acid ester, 0.5 wt % of trifluoromethanesulfonic acid, up to 5 wt ppm of phosphorus, and 510 wt ppm of free fluorine. The actual amount of trifluoromethanesulfonic acid anhydride produced by the reaction was 34.3 kg, and the yield was 73%, based on the amount of trifluoromethanesulfonic acid.

Then, 190 kg of 100% phosphoric acid was added to the residue of the first distillation. Then, the second distillation of Example 1 was repeated, thereby to obtain 1.9 kg of trifluoromethanesulfonic acid anhydride which is colorless and transparent. By chemical analysis, this second distillate was found to have a purity of at least 99% and contain up to 0.5 wt % of trifluoromethanesulfonic acid ester, up to 0.5 wt % of trifluoromethanesulfonic acid, up to 5 wt ppm of phosphorus, and 480 wt ppm of free fluorine. The yield was 4%, based on the amount of trifluoromethanesulfonic acid. Thus, the total yield was 77%.

EXAMPLE 5

In this example, Example 1 was modified as follows. At first, a reactor that is the same as that of Example 1 was charged with 320 kg of a trifluoromethanesulfonic acid anhydride that has a purity of 93 wt % and contains 5 wt % of trifluoromethanesulfonic acid aster, 2 wt % of trifluoromethanesulfonic acid, 70 wt ppm of phosphorus, and 630 ppm of free fluorine. Then, 80 kg (9 moles per 6 moles of trifluoromethanesulfonic acid) of diphosphorus pentoxide was added to the solvent in the same manner as that of Example 1. Then, to this slurry containing 20 wt % of diphosphorus pentoxide 50 kg of trifluoromethanesulfonic acid was added. Then, this reaction mixture was maintained at 10° C. for 8 hr to conduct the reaction. In this reaction, conversion of trifluoromethanesulfonic acid was 99.5%.

Then, the first distillation of Example 1 was repeated, thereby to obtain 350.5 kg of trifluoromethanesulfonic acid anhydride which is colorless and transparent. By chemical analysis, this first distillate was found to have a purity of 97 wt % and contain 2.9 wt % of trifluoromethanesulfonic acid ester, up to 0.5 wt % of trifluoromethanesulfonic acid, up to 5 wt ppm of phosphorus, and 590 wt ppm of free fluorine. The actual amount of trifluoromethanesulfonic acid anhydride produced by the reaction was 42.4 kg, and the yield was 80%, based on the amount of trifluoromethanesulfonic acid.

Then, 184 kg of 100% phosphoric acid was added to the residue of the first distillation. Then, the second distillation of Example 1 was repeated, thereby to obtain 2.1 kg of trifluoromethanesulfonic acid anhydride which is colorless and transparent. By chemical analysis, this second distillate was found to have a purity of at least 99% and contain up to 0.5 wt % of trifluoromethanesulfonic acid ester, up to 0.5 wt % of trifluoromethanesulfonic acid, up to 5 wt ppm of phosphorus, and 550 wt ppm of free fluorine. The yield was 4%, based on the amount of trifluoromethanesulfonic acid. Thus, the total yield was 84%.

EXAMPLE 6

In this example, Example 1 was modified as follows. At first, a reaction mixture that is the same as that of Example 1 was maintained in the same manner as that of Example 1, in order to conduct the reaction. In this reaction, conversion of trifluoromethanesulfonic acid was 99.5%.

Then, the first distillation of Example 1 was repeated, thereby to obtain 358.5 kg of trifluoromethanesulfonic acid anhydride which is colorless and transparent. By chemical analysis, this first distillate was found to have the same purity and the same impurity concentrations as those of the first distillate of Example 1. The actual amount of trifluoromethanesulfonic acid anhydride produced by the reaction was 38.5 kg, and the yield was 82%, based on the amount of trifluoromethanesulfonic acid.

To the residue remaining after the first distillation, 192 kg of a phosphoric acid was added. This phosphoric acid contained 2 wt % of trifluoromethanesulfonic acid and 98 wt % of phosphoric acid and was prepared by adding water to the residue (pyrophosphoric acid) remaining after the second distillation of Example 1. Then, the second distillation of Example 1 was repeated, thereby to obtain 1.9 kg of trifluoromethanesulfonic acid anhydride which is colorless and transparent. By chemical analysis, this second distillate was found to have the same purity and the same impurity concentrations as those of the second distillate of Example 1. The yield was 4%, based on the amount of trifluoromethanesulfonic acid. Thus, the total yield was 86%.

EXAMPLE 7

In this example, Example 1 was modified as follows. At first, a reaction mixture that is the same as that of Example 1 was maintained in the same manner as that of Example 1, in order to conduct the reaction. In this reaction, conversion of trifluoromethanesulfonic acid was 99.5%.

Then, the first distillation of Example 1 was repeated, thereby to obtain 357.6 kg of trifluoromethanesulfonic acid anhydride which is colorless and transparent. By chemical analysis, this first distillate was found to have the same purity and the same impurity concentrations as those of the first distillate of Example 1, except that the free fluorine concentration was 490 wt ppm. The actual amount of trifluoromethanesulfonic acid anhydride produced by the reaction was 37.6 kg, and the yield was 80%, based on the amount of trifluoromethanesulfonic acid To the residue remaining after the first distillation, 202 kg of a phosphoric acid was added. This phosphoric acid contained 2 wt % of trifluoromethanesulfonic acid, 5 wt % of water, and 93 wt % of phosphoric acid and was prepared by adding water to the residue remaining after the second distillation of Example 6. Then, the second distillation of Example 1 was repeated, thereby to obtain 0.9 kg of trifluoromethanesulfonic acid anhydride which is colorless and transparent. By chemical analysis, this second distillate was found to have the same purity and the same impurity concentrations as those of the second distillate of Example 1, except that the free fluorine concentration was 520 ppm. The yield was 2%, based on the amount of trifluoromethanesulfonic acid. Thus, the total yield was 82%.

EXAMPLE 8

In this example, Example 1 was modified as follows. At first, a reactor that is the same as that of Example 1 was charged with 320 kg of a trifluoromethanesulfonic acid anhydride that is the same as that of Example 1. Then, 50 kg of trifluoromethanesulfonic acid was added to the solvent, while the solvent was maintained at 5° C., by allowing cold water to flow through the coil, with stirring. Then, 80 kg (10 moles per 6 moles of trifluoromethanesulfonic acid) of diphosphorus pentoxide was added to this mixture with stirring. Then, this reaction mixture was maintained at 10° C. for 12 hr to conduct the reaction. In this reaction, conversion of trifluoromethanesulfonic acid was 97%.

Then, the first distillation of Example 1 was repeated, thereby to obtain 360.3 kg of trifluoromethanesulfonic acid anhydride which is colorless and transparent. By chemical analysis, this first distillate was found to have a purity of 99 wt % and contain 1 wt % of trifluoromethanesulfonic acid ester, up to 0.5 wt % of trifluoromethanesulfonic acid, up to 5 wt ppm of phosphorus, and 570 wt ppm of free fluorine. The actual amount of trifluoromethanesulfonic acid anhydride produced by the reaction was 36.7 kg, and the yield was 78%, based on the amount of trifluoromethanesulfonic acid.

Then, 188 kg of 100% phosphoric acid was added to the residue of the first distillation. Then, the second distillation of Example 1 was repeated, thereby to obtain 1.9 kg of trifluoromethanesulfonic acid anhydride which is colorless and transparent. By chemical analysis, this second distillate was found to have the same purity and the same impurity concentrations, except that the free fluorine concentration was 520 wt ppm. The yield was 4%, based on the amount of trifluoromethanesulfonic acid. Thus, the total yield was 82%.

EXAMPLE 9

In this example, Example 1 was modified as follows. At first, a reaction mixture was prepared in the same manner as that of Example 1, except that 320 kg of n-$C_9F_{20}$ having a purity of at least 99 wt % was used as the fluorine-containing solvent. The reaction mixture was maintained in the same manner as that of Example 1, in order to conduct the reaction. In this reaction, conversion of trifluoromethanesulfonic acid was 99.5%.

Then, a mixture of n-$C_9F_{20}$ and trifluoromethanesulfonic acid anhydride was distilled off by simple distillation from the reaction mixture under a pressure of 50 torr, by raising the temperature from 45° C. to 200° C., with the heat medium's flow through the jacket. This distillation was continued until the end of boiling of this mixture, thereby to obtain 342.5 kg of a first distillate. By chemical analysis, the first distillate was found to contain up to 0.5 wt % of trifluoromethanesulfonic acid ester, up to 0.5 wt % of trifluoromethanesulfonic acid, up to 5 wt ppm of phosphorus, 70 wt ppm of free fluorine, 88.8 wt % of n-$C_9F_{20}$, and 11.2 wt % of trifluoromethanesulfonic acid anhydride. In this first distillation, 304 kg of n-$C_9F_{20}$ was recovered, and thus the recovery was 95%. In contrast, 38.4 kg of trifluoromethanesulfonic acid anhydride was obtained in the first distillation, and the yield wad 82%.

Then, 188 kg of 100% phosphoric acid was added to the residue of the first distillation. Then, a mixture of trifluoromethanesulfonic acid anhydride and n-$C_9F_{20}$ was again distilled off by simple distillation from the reaction mixture under a pressure of 50 torr by raising the temperature from 45° C. to 200° C. With this, there was obtained 11.5 kg of a second distillate. By chemical analysis, the second distillate was found to contain up to 0.5 wt % of trifluoromethanesulfonic acid ester, up to 0.5 wt % of trifluoromethanesulfonic acid, up to 5 wt ppm of phosphorus, 80 wt ppm of free fluorine, 83.5 wt % of n-$C_9F_{20}$, and 16.5 wt % of trifluoromethanesulfonic acid anhydride. In this second distillation, 9.6 kg of n-$C_9F_{20}$ was recovered. Thus, the recovery was 3% in the second distillation, and the total recovery was 98%. In contrast, 1.9 kg of trifluoromethanesulfonic acid anhydride was obtained in the second distillation, and the yield was 4%. Thus, the total yield was 86%.

Then, 354 kg of the total of the first and second distillates (the crude reaction products) was rectified under a pressure of 160 torr at 45° C. In this rectification, refluxing was conducted for 1 hr. After cutting out 7 kg of the initial distillate, the middle distillate was taken out, thereby to obtain 25 kg of a rectified product which is colorless and transparent. By chemical analysis, this rectified product was found to contain up to 0.5 wt % of trifluoromethanesulfonic acid ester, up to 0.5 wt % of trifluoromethanesulfonic acid, up to 5 wt ppm of phosphorus, 10 wt ppm of free fluorine, up to 0.2 wt % of n-$C_9F_{20}$, and at least 99wt % of trifluoromethanesulfonic acid anhydride. The initial distillate of the rectification and the crude trifluoromethanesulfonic acid anhydride of the remaining liquid in the reactor were usable as the fluorine containing solvent.

EXAMPLE 10

In this example, Example 1 was modified as follows. At first, a reaction mixture was prepared in the same manner as that of Example 1, except that 320 kg of $(C_3F_7)_3N$ having a purity of at least 99 wt % was used as the fluorine-containing solvent. The reaction mixture was maintained in the same manner as that of Example 1, in order to conduct the reaction. In this reaction, conversion of trifluoromethanesulfonic acid was 99.5%.

Then, the first distillation of Example 9 was repeated to distill off a mixture of $(C_3F_7)_8N$ and trifluoromethanesulfonic acid anhydride, thereby to obtain 338.6 kg of a first distillate By chemical analysis, the first distillate was found to contain up to 0.5 wt % of trifluoromethanesulfonic acid ester, up to 0.5 wt % of trifluoromethanesulfonic acid, up to 5 wt ppm of phosphorus, 90 wt ppm of free fluorine, 88.9 wt % of $(C_9F_7)_3N$, and 11.1 wt % of trifluoromethanesulfonic acid anhydride. In this first distillation, 301 kg of $(C_3F_7)_3N$ was recovered, and thus the recovery was 94%. In contrast, 37.6 kg of trifluoromethanesulfonic acid anhydride was obtained in the first distillation, and the yield wad 80%.

Then, 188 kg of 100% phosphoric acid was added to the residue of the first distillation. Then, the second distillation of Example 9 was repeated, thereby to obtain 18.4 kg of a second distillate. By chemical analysis, the second distillate was found to contain up to 0.5 wt % of trifluoromethanesulfonic acid ester, up to 0.5 wt % of trifluoromethanesulfonic acid, up to 5 wt ppm of phosphorus, 90 wt ppm of free fluorine, 87 wt % of $(C_3F_7)_3N$, and 13 wt % of trifluoromethanesulfonic acid anhydride. In this second distillation, 16 kg of $(C_3F_7)_9N$ was recovered. Thus, the recovery was 5% in the second distillation, and the total recovery was 99%. In contrast, 2.4 kg of trifluoromethanesulfonic acid anhydride was obtained in the second distillation, and the yield was 5%. Thus, the total yield was 85%.

Then, 357 kg of the total of the first and second distillates (the crude reaction products) was rectified in the same manner as that of Example 9, thereby to obtain 27 kg of a rectified product which is colorless and transparent. By chemical analysis, this rectified product was found to contain up to 0.5 wt % of trifluoromethanesulfonic acid ester, up to 0.5 wt % of trifluoromethanesulfonic acid, up to 5 wt ppm of phosphorus, 20 wt ppm of free fluorine, up to 0.2 wt % of $(C_3F_7)_3N$, and at least 99 wt % of trifluoromethanesulfonic acid anhydride. The initial distillate of the rectification, the crude trifluoromethanesulfonic acid anhydride and $(C_3F_7)_3N$ of the remaining liquid in the reactor were usable as the fluorine-containing solvent.

COMPARATIVE EXAMPLE 1

In this comparative example, the fluorine-containing solvent was omitted, as follows. At first, a reactor that is the same as that of Example 1 was charged with 200 kg of trifluoromethanesulfonic acid. Then, 160 kg (5.1 moles per 6 moles of trifluoromethanesulfonic acid) of diphosphorus pentoxide was added to the trifluoromethanesulfonic acid, while the trifluoromethanesulfonic acid was maintained at 5° C., by allowing cold water to flow through the coil, with stirring. Then, this reaction mixture was maintained at 10° C. to conduct the reaction. After a lapse of 1 hr from the start of the reaction, the reaction mixture (slurry) solidified. Therefore, the reaction was terminated. In this reaction, conversion of trifluoromethanesulfonic acid was 71%.

Then, the first distillation of Example 1 was repeated, thereby to obtain 121 kg of trifluoromethanesulfonic acid anhydride which is colorless and transparent. By chemical analysis, this first distillate was found to have a purity of 93 wt % and contain 5 wt % of trifluoromethanesulfonic acid ester, 2 wt % of trifluoromethanesulfonic acid, 50 wt ppm of phosphorus, and 600 wt ppm of free fluorine. The amount of trifluoromethanesulfonic acid anhydride produced by the reaction was 112.5 kg, and the yield was 59.8%, based on the amount of trifluoromethanesulfonic acid.

EXAMPLE 11

In this example, Example 1 was modified, as follows. At first, a reaction mixture reactor that is the same as that of Example 1 was charged with 200 kg of trifluoromethanesulfonic acid. Then, 120 kg (3.8 moles per 6 moles of trifluoromethanesulfonic acid) of diphosphorus pentoxide was added to the trifluoromethanesulfonic acid in the same manner as that of Comparative Example 1. Then, this reaction mixture was maintained at 10° C. to conduct the reaction. After a lapse of 1 hr from the start of the reaction, the reaction mixture (slurry) solidified. Therefore, the reaction was terminated. In this reaction, conversion of trifluoromethanesulfonic acid was 70%.

Then, the first distillation of Example 1 was repeated, thereby to obtain 118.5 kg of trifluoromethanesulfonic acid anhydride which is colorless and transparent. By chemical analysis, this first distillate was found to have a purity of 92 wt % and contains 6 wt % of trifluoromethanesulfonic acid ester, 2 wt % of trifluoromethanesulfonic acid, 60 wt ppm of phosphorus, and 640 wt ppm of free fluorine. The amount of trifluoromethanesulfonic acid anhydride produced by the reaction was 109.0 kg, and the yield was 58%, based on the amount of trifluoromethanesulfonic acid.

Then, 240 kg of 100% phosphoric acid was added to the is residue of the first distillation. Then, trifluoromethanesulfonic acid anhydride was again distilled off by simple distillation from the reaction mixture under a pressure of 160 torr by raising the temperature from 45° C. to 90° C. With this, there was obtained 13.3 kg of trifluoromethanesulfonic acid anhydride which is colorless and transparent. By chemical analysis, this second distillate was found to have a purity of 99 wt % and contain 1 wt % of trifluoromethanesulfonic acid ester, up to 0.5 wt % of trifluoromethanesulfonic acid, up to 5 wt ppm of phosphorus, and 550 wt ppm of free fluorine. The yield was 7%, based on the amount of trifluoromethanesulfonic acid. Thus, the total yield was 65%.

The residue remaining after the second distillation was polyphosphoric acid in the form of liquid at 90° C., and thus it was possible to easily purge this residue from the reactor.

Separately, 131.8 kg of the obtained crude trifluoromethanesulfonic acid anhydride was rectified in the same manner as that of Example 1, except that 40 kg of the initial distillate was cut out. With this, there was obtained 49 kg of a rectified product which is colorless and transparent. By chemical analysis, this rectified product was found to have a purity of at least 99 wt % and contain 0.8 wt % of trifluoromethanesulfonic acid ester, up to 0.5 wt % of trifluoromethanesulfonic acid, up to 5 wt ppm of phosphorus, and 90 wt ppm of free fluorine.

EXAMPLE 12

In this example, Example 1 was modified as follows. At first, a reaction mixture was prepared in the same manner as that of Example 1, by adding trifluoromethanesulfonic acid to the diphosphorus pentoxide slurry. Then, this reaction mixture was maintained at 140° C., to conduct the reaction. 2 hr after the start of the reaction, the reaction mixture (slurry) solidified. Therefore, the reaction was terminated. In this reaction, conversion of trifluoromethanesulfonic acid was 87%.

Then, the first distillation of Example 1 was repeated, thereby to obtain 363.8 kg of trifluoromethanesulfonic acid anhydride which is colorless and transparent. By chemical analysis, this first distillate was found to have a purity of 97 wt % and contain 2 wt % of trifluoromethanesulfonic acid ester, 1 wt % of trifluoromethanesulfonic acid, up to 5 wt ppm of phosphorus, and 2,440 wt ppm of free fluorine. The actual amount of trifluoromethanesulfonic acid anhydride produced by the reaction was 32.9 kg, and the yield was 70%, based on the amount of trifluoromethanesulfonic acid.

Then, 190 kg of 100% phosphoric acid was added to the residue of the first distillation. Then, the second distillation of Example 1 was repeated, thereby to obtain 2.9 kg of trifluoromethanesulfonic acid anhydride which is colorless and transparent. By chemical analysis, this second distillate was found to have a purity of at least 99% and contain up to 0.5 wt % of trifluoromethanesulfonic acid ester, up to 0.5 wt % of trifluoromethanesulfonic acid, up to 5 wt ppm of phosphorus, and 870 wt ppm of free fluorine. The yield was 6%, based on the amount of trifluoromethanesulfonic acid. Thus, the total yield was 76%.

EXAMPLE 13

At first, a reactor that is equipped with a jacket, a coil and a stirrer and made of Hastelloy-C, and has a capacity of 0.3 m$^3$ was charged with 320 kg of $(C_4F_9SO_2)_2O$ that has a purity of at least 99 wt % and contains up to 0.5 wt % of $C_nF_{2n+1}SO_2.OC_nF_{2n+1}$ where n is an integer from 1 to 4, up to 0.5 wt % of $C_nF_{2n+1}SO_3H$ where n is an integer from 1 to 4, up to 5 wt ppm of phosphorus, and 35 wt ppm of free fluorine. Then, 80 kg (20.3 moles per 6 moles of $C_4F_9SO_3H$) of diphosphorus pentoxide was added to the solvent, while the solvent was maintained at 5° C., by allowing cold water to flow through the coil, with stirring. Then, to this slurry containing 20 wt % of diphosphorus pentoxide 50 kg of $C_4F_9SO_3H$ was added. Then, this reaction mixture was maintained at 10° C. for 10 hr with sufficient stirring to conduct the reaction. In this reaction, conversion of $C_4F_9SO_3H$ was 99%.

Then, $(C_4F_9SO_2)_2O$ was distilled off by simple distillation from the reaction mixture under a pressure of 10 torr by raising the temperature from 65° C. to 200° C. with the heat medium flow through the jacket. This distillation was continued until the end of boiling of $(C_4F_9SO_2)_2O$, thereby to obtain 355.4 kg of $(C_4F_9SO_2)_2O$ which is colorless and transparent. By chemical analysis, this first distillate was found to have a purity of at least 99 wt % and contain up to 0.5 wt % of fluoroalkylsulfonic acid ester, up to 0.5 wt % of fluoroalkylsulfonic acid, 150 wt ppm of phosphorus, and 1,550 wt ppm of free fluorine. The actual amount of $(C_4F_9SO_2)_2O$ produced by the reaction was 35.4 kg, and the yield was 73%, based on the amount of $C_4F_9SO_3H$.

Then, 205 kg of 100% phosphoric acid was added to the residue of the above simple distillation. Then, $(C_4F_9SO_2)_2O$ was again distilled off by simple distillation from the reaction mixture under a pressure of 10 torr by raising the temperature from 65° C. to 120° C. With this, there was obtained 2.9 kg of $(C_4F_9SO_2)_2O$ which is colorless and transparent. By chemical analysis, this second distillate was found to have a purity of at least 99 wt % and contain up to 0.5 wt % of fluoroalkylsulfonic acid ester, up to 0.5 wt % of fluoroalkylsulfonic acid, 60 wt ppm of phosphorus, and 880 wt ppm of free fluorine. The yield was 6%, based on the amount of $C_4F_9SO_3H$. Thus, the total yield was 79%.

The residue remaining after the second distillation was polyphosphoric acid in the form of liquid at 90° C., and thus it was possible to easily purge this residue from the reactor.

Separately, 358.3 kg of the obtained crude $(C_4F_9SO_2)_2O$ was rectified under a pressure of 10 torr at 65° C., in order to reduce the free fluorine concentration thereof. In this rectification, refluxing was conducted for 1 hr. After cutting out 36 kg of the initial distillate, the middle distillate was taken out, thereby to obtain 215 kg of a rectified product which is colorless and transparent. By chemical analysis, this rectified product was found to have a purity of at least 99 wt % and contain up to 0.5 wt % of fluoroalkylsulfonic acid ester, up to 0.5 wt % of fluoroalkylsulfonic acid, up to 5 wt ppm of phosphorus, and 35 wt ppm of free fluorine. The initial distillate of the rectification and the crude $(C_4F_9SO_2)_2O$ of the remaining liquid in the reactor were usable as the fluorine-containing solvent.

COMPARATIVE EXAMPLE 2

In this comparative example, the fluorine-containing solvent was omitted, as follows. At first, a reactor that is the same as that of Example 13 was charged with 200 kg of $C_4F_9SO_3H$ having a purity of at least 99%. Then, 160 kg (10.2 moles per 6 moles of $C_4F_9SO_3H$) of diphosphorus pentoxide was added to $C_4F_9SO_3H$, while $C_4F_9SO_3H$ was maintained at 5° C., by allowing cold water to flow through the coil, with stirring. Then, this reaction mixture was maintained at 10° C. to conduct the reaction. After a lapse of 50 minutes from the start of the reaction, the reaction mixture (slurry) solidified. Therefore, the reaction was terminated. In this reaction, conversion of $C_4F_9SO_3H$ was 62%.

Then, the first distillation of Example 13 was repeated, thereby to obtain 93.9 kg of $(C_4F_9SO_2)_2O$ which is colorless and transparent. By chemical analysis, this distillate was found to have a purity of 93 wt % and contain 4 wt % of $C_4F_9SO_2.OC_4F_9$, 2 wt % of $C_3F_7SO_2.OC_3F_7$, up to 0.5 wt % of $C_2F_5SO_2.OC_2F_5$, up to 0.5 wt % of $CF_3SO_2.OCF_3$, 1 wt % of $C_4F_9SO_3H$, up to 0.5 wt % of $C_3F_7SO_3H$, up to 0.5 wt % of $C_2F_5SO_3H$, up to 0.5 wt % of $CF_3SO_3H$, 170 wt ppm of phosphorus, and 1,620 wt ppm of free fluorine. The amount of $(C_4F_9SO_2)_2O$ produced by the reaction was 87.3 kg, and the yield was 45%, based on the amount of $C_4F_9SO_3H$.

EXAMPLE 14

At first, a reactor that is the same as that of Example 13 was charged with 320 kg of $(C_8F_{17}SO_2)_2O$ that has a purity of at least 99 wt % and contains up to 0.5 wt % of $C_nF_{2n+1}SO_2.OC_nF_{2n+1}$ where n is an integer from 1 to 8, up to 0.5 wt % of $C_nF_{2n+1}SO_3H$ where n is an integer from 1 to 8, 100 wt ppm of phosphorus, and 860 wt ppm of free fluorine. Then, 80 kg (33.8 moles per 6 moles of $C_8F_{17}SO_3H$) of diphosphorus pentoxide was added to the solvent, while the solvent was maintained at 40° C., by allowing water to flow through the coil, with stirring. Then, to this slurry containing 20 wt % of diphosphorus pentoxide 50 kg of $C_8F_{17}SO_3H$ having a purity of at least 99% was added. Then, this reaction mixture was maintained at 40° C. for 16 hr with sufficient stirring to conduct the reaction. In this reaction, conversion of $C_8F_{17}SO_3H$ was 95%.

Then, $(C_8F_{17}SO_2)_2O$ was distilled off by simple distillation from the reaction mixture under a pressure of 10 torr by raising the temperature from 115° C. to 250° C. with the heat medium flow through the jacket. This distillation was continued until the end of boiling of $(C_8F_{17}SO_2)_2O$, thereby to obtain 351.9 kg of $(C_8F_{17}SO_2)_2O$ which is colorless and transparent. By chemical analysis, this first distillate was found to have a purity of at least 99 wt % and contain up to 0.5 wt % of fluoroalkylsulfonic acid ester, up to 0.5 wt % of fluoroalkylsulfonic acid, 550 wt ppm of phosphorus, and 3,700 wt ppm of free fluorine. The actual amount of $(C_8F_{17}SO_2)_2O$ produced by the reaction was 31.9 kg, and the yield was 65%, based on the amount of $C_8F_{17}SO_3H$.

Then, 211 kg of 100% phosphoric acid was added to the residue of the above simple distillation. Then, $(C_8F_{17}SO_2)_2O$ was again distilled off by simple distillation from the reaction mixture under a pressure of 10 torr by raising the temperature from 115° C. to 170° C. With this, there was obtained 2.1 kg of $(C_8F_{17}SO_2)_2O$ which is colorless and transparent. By chemical analysis, this second distillate was found to have a purity of at least 99 wt % and contain up to 0.5 wt % of fluoroalkylsulfonic acid ester, up to 0.5 wt % of fluoroalkylsulfonic acid, 460 wt ppm of phosphorus, and 2,350 wt ppm of free fluorine. The yield was 4%, based on the amount of $C_8F_{17}SO_3H$. Thus, the total yield was 69%.

The residue remaining after the second distillation was polyphosphoric acid in the form of liquid at 90° C., and thus it was possible to easily purge this residue from the reactor.

Separately, 354 kg of the obtained crude $(C_8F_{17}SO_2)_2O$ was rectified under a pressure of 10 torr at 115° C., in order to reduce the free fluorine concentration thereof. In this rectification, refluxing was conducted for 1 hr. After cutting out 35 kg of the initial distillate, the middle distillate was taken out, thereby to obtain 210 kg of a rectified product which is colorless and transparent. By chemical analysis, this rectified product was found to have a purity of at least 99 wt % and contain up to 0.5 wt % of fluoroalkylsulfonic acid ester, up to 0.5 wt % of fluoroalkylsulfonic acid, 100 wt ppm of phosphorus, and 860 wt ppm of free fluorine. The initial distillate of the rectification and the crude $(C_8F_{17}SO_2)_2O$ of the remaining liquid in the reactor were usable as the fluorine-containing solvent.

COMPARATIVE EXAMPLE 3

In this example, the fluorine-containing solvent was omitted, as follows. At first, a reactor that is the same as that of Example 13 was charged with 200 kg of $C_8F_{17}SO_3H$. Then, 160 kg (16.9 moles per 6 moles of $C_8F_{17}SO_3H$) of diphosphorus pentoxide was added to $C_8F_{17}SO_3H$, while $C_8F_{17}SO_3H$ was maintained at 40° C., by allowing water to flow through the coil, with stirring. Then, this reaction mixture was maintained at 40° C. to conduct the reaction. After a lapse of 40 minutes from the start of the reaction, the reaction mixture (slurry) solidified. Therefore, the reaction was terminated. In this reaction, conversion of $C_8F_{17}SO_3H$ was 48%.

Then, the first distillation of Example 14 was repeated, thereby to obtain 79.9 kg of $(C_8F_{17}SO_2)_2O$ which is colorless and transparent. By chemical analysis, this first distillate was found to have a purity of 91 wt % and contain 5 wt % of $C_8F_{17}SO_2.OC_8F_{17}$, 2 wt % of $C_7F_{15}SO_2.OC_7F_{15}$, up to 0.5 wt % of $C_6F_{13}SO_2.OC_6F_{13}$, 2 wt % of $C_8F_{17}SO_3H$, up to 0.5 wt % of $C_7F_{15}SO_3H$, 620 wt ppm of phosphorus, and 4,100 wt ppm of free fluorine. The amount of $(C_8F_{17}SO_2)_2O$ produced by the reaction was 72.7 kg, and the yield was 37%, based on the amount of $C_8F_{17}SO_3H$.

EXAMPLE 15

At first, a reactor that is made of stainless steel (SUS304) and equipped with a jacket and a stirrer and has a capacity of 0.27 m³ was charged with 240 kg of a trifluoromethanesulfonic acid anhydride (fluorine-containing solvent) that has a purity of at least 99 wt % and contains up to 0.5 wt % of trifluoromethanesulfonic acid ester, up to 0.5 wt % of trifluoromethanesulfonic acid, up to 5 wt ppm of phosphorus, and 350 wt ppm of free fluorine. Then, 100 kg of trifluoromethanesulfonic acid was added to the reactor. Then, 75 kg (4.75 moles per 6 moles of trifluoromethanesulfonic acid) of diphosphorus pentoxide was intermittently added five times in parts to the reactor, while the solution mixture was maintained at 25° C., by allowing heat medium to flow through the jacket, with stirring In fact, 15 kg of diphosphorus pentoxide was added at each time in three hours, and the reaction mixture was maintained for 15 hr at 30° C. with sufficient stirring to conduct the reaction. In this reaction, conversion of trifluoromethanesulfonic acid was 95%.

Then, trifluoromethanesulfonic acid anhydride was distilled off by simple distillation from the reaction mixture under a pressure of 160 torr by raising the temperature from 45° C. to 160° C. with the heat medium flow through the jacket. This distillation was continued until the end of boiling of trifluoromethanesulfonic acid anhydride, thereby to obtain 315.2 kg of trifluoromethanesulfonic acid anhydride which is colorless and transparent. By chemical analysis, this first distillate was found to have a purity of at least 99 wt % and contain up to 0.5 wt % of trifluoromethanesulfonic acid ester, up to 0.5 wt % of trifluoromethanesulfonic acid, up to 5 wt ppm of phosphorus, and 300 wt ppm of free fluorine The actual amount of trifluoromethanesulfonic acid anhydride produced by the reaction was 75.2 kg, and the yield was 80%, based on the amount of trifluoromethanesulfonic acid.

Then, 275 kg of 100% phosphoric acid was added to the residue of the above simple distillation. Then, trifluoromethanesulfonic acid anhydride was again distilled off by simple distillation from the reaction mixture under a pressure of 160 torr by raising the temperature from 45° C. to 90° C. With this, there was obtained 4.1 kg of trifluoromethanesulfonic acid anhydride which is colorless and transparent. By chemical analysis, this second distillate was found to have the same purity and the same impurity concentrations as those of the first distillate, except that the free fluorine concentration was 350 ppm. The yield was 4%, based on the amount of trifluoromethanesulfonic acid. Thus, the total yield was 84%.

The residue remaining after the second distillation was completely dissolved by adding 100% phosphoric acid thereto. The thus dissolved residue was polyphosphoric acid in the form of liquid at 90° C., and it was possible to easily purge the residue from the reactor.

Separately, 319.3 kg of the obtained crude trifluoromethanesulfonic acid anhydride was rectified under a pressure of 160 torr at 45° C., in order to reduce the free fluorine concentration thereof. In this rectification, refluxing was conducted for 1 hr. After cutting out 16 kg of the initial distillate, the middle distillate was taken out, thereby to obtain 224 kg of a rectified product which is colorless and transparent. By chemical analysis, this rectified product was found to have a purity of at least 99 wt % and contain up to 0.5 wt % of trifluoromethanesulfonic acid ester, up to 0.5 wt % of trifluoromethanesulfonic acid, up to 5 wt ppm of phosphorus, and 35 wt ppm of free fluorine. The initial distillate of the rectification and the crude trifluoromethanesulfonic acid anhydride of the remaining liquid in the reactor were usable as the fluorine-containing solvent.

EXAMPLE 16

At first, a reactor that is the same as that of Example 15 was charged with 240 kg of a trifluoromethanesulfonic acid anhydride having the same purity and the same impurity concentrations as those of Example 15, except that the free fluorine concentration was 300 wt ppm. Then, 100 kg of trifluoromethanesulfonic acid having a purity of at least 99 wt % was added to the reactor. Then, 75 kg (4.75 moles per 6 moles of trifluoromethanesulfonic acid) of diphosphorus pentoxide was intermittently added three times in parts to the reactor, while the solution mixture was maintained at 25° C., by allowing heat medium to flow through the jacket, with stirring. In fact, 15 kg of diphosphorus pentoxide was added at each time in three hours, and thus the reaction mixture was maintained for 9 hr at 30° C. with sufficient stirring to conduct the reaction. After the reaction, it was found that conversion of trifluoromethanesulfonic acid was 85%. Therefore, the reaction mixture was further stirred for 6 hr. After this stirring, its conversion increased to 90%.

Then, the procedure of the first distillation of Example 15 was repeated, thereby to obtain 306.7 kg of trifluoromethanesulfonic acid anhydride which is colorless and transparent. By chemical analysis, this first distillate was found to have the same purity and the same impurity concentrations as those of the above trifluoromethanesulfonic acid anhydride used as the solvent, except that the free fluorine concentration was 310 wt ppm. The actual amount of trifluoromethanesulfonic acid anhydride produced by the reaction was 66.7 kg, and the yield was 71%, based on the amount of trifluoromethanesulfonic acid.

Then, 275 kg of 100% phosphoric acid was added to the residue of the above simple distillation. Then, the second distillation of Example 15 was repeated, thereby to obtain 3.8 kg of trifluoromethanesulfonic acid anhydride which is colorless and transparent. By chemical analysis, this second distillate was found to have the same purity and the same impurity concentrations as those of the first distillate, except that the free fluorine concentration was 350 ppm. The yield was 4%, based on the amount of trifluoromethanesulfonic acid. Thus, the total yield was 75%.

EXAMPLE 17

At first, a reactor that is the same as that of Example 15 was charged with 240 kg of a trifluoromethanesulfonic acid anhydride having the same purity and the same impurity concentrations as those of Example 16. Then, 100 kg of trifluoromethanesulfonic acid having a purity of at least 99 wt % was added to the reactor. Then, 75 kg (4.75 moles per 6 moles of trifluoromethanesulfonic acid) of diphosphorus pentoxide was intermittently added to the reactor, in the same manner as that of Example 15, to conduct the reaction. In this reaction, conversion of trifluoromethanesulfonic acid was 96%.

Then, the procedure of the first distillation of Example 15 was repeated, thereby to obtain 317.1 kg of trifluoromethanesulfonic acid anhydride which is colorless and transparent. By chemical analysis, this first distillate was found to have the same purity and the same impurity concentrations as those of the above trifluoromethanesulfonic acid anhydride used as the solvent. The actual amount of trifluoromethanesulfonic acid anhydride produced by the reaction was 77.1 kg, and the yield was 82%, based on the amount of trifluoromethanesulfonic acid.

Then, 275 kg of a phosphoric acid was added to the residue of the above first distillation. This phosphoric acid was made up of 3 wt % of trifluoromethanesulfonic acid, 6 wt % of water, and 91 wt % of phosphoric acid, and was prepared by adding water to a polyphosphoric acid produced from the residue of Example 15. Then, the procedure of the second distillation of Example 15 was repeated, thereby to obtain 1.7 kg of trifluoromethanesulfonic acid anhydride which is colorless and transparent. By chemical analysis, this second distillate was found to have the same purity and the same impurity concentrations as those of the first distillate, except that the free fluorine concentration was 330 ppm. The yield was 2%, based on the amount of trifluoromethanesulfonic acid. Thus, the total yield was 84%.

The residue remaining after the second distillation was completely dissolved by adding the reused phosphoric acid thereto. The thus dissolved residue was polyphosphoric acid in the form of liquid at 90° C., and it was possible to easily purge the residue from the reactor.

EXAMPLE 18

At first, a reactor that is the same as that of Example 15 was charged with 240 kg of n-$C_9F_{20}$ having a purity of at least 99 wt %. Then, 100 kg of trifluoromethanesulfonic acid having a purity of at least 99 wt % was added to the reactor. Then, 75 kg (4.75 moles per 6 moles of trifluoromethanesulfonic acid) of diphosphorus pentoxide was intermittently added to the reactor, in the same manner as that of Example 15, to conduct the reaction. In this reaction, conversion of trifluoromethanesulfonic acid was 94%.

Then, a mixture of n-$C_9F_{20}$ and trifluoromethanesulfonic acid anhydride was distilled off by simple distillation from the reaction mixture, under a pressure of 50 torr, by raising the temperature from 45° C. to 200° C., with the heat medium flow through the jacket. This distillation was continued until the end of boiling of these compounds, thereby to obtain 304.1 kg of a first distillate. By chemical analysis, this first distillate was found to contain up to 0.5 wt % of trifluoromethanesulfonic acid ester, up to 0.5 wt % of trifluoromethanesulfonic acid, up to 5 wt ppm of phosphorus, 70 wt ppm of free fluorine, 75.0 wt % of n-$C_9F_{20}$, and 25.0 wt % of trifluoromethanesulfonic acid anhydride. In this first distillation, 228 kg of a-$C_9F_{20}$ was recovered, and thus the recovery was 95%. In contrast, 76.1 kg of trifluoromethanesulfonic acid anhydride was obtained in the first distillation, and the yield was 81%.

Then, 275 kg of 100% phosphoric acid was added to the residue of the first distillation. Then, a second distillation (simple distillation) was conducted under a pressure of 50 torr, by raising the temperature from 45° to 200° C., thereby to obtain 11.0 kg of a second distillate. By chemical analysis, the second distillate was found to contain up to 0.5 wt % of trifluoromethanesulfonic acid ester, up to 0.5 wt % of trifluoromethanesulfonic acid, up to 5 wt ppm of phosphorus, 80 wt ppm of free fluorine, 65.5 wt % of n-$C_9F_{20}$, and 34.5 wt % of trifluoromethanesulfonic acid anhydride. In this second distillation, 7.2 kg of n-$C_9F_{20}$ was recovered. Thus, the recovery was 3% in the second distillation, and the total recovery was 98%. In contrast, 3.8 kg of trifluoromethanesulfonic acid anhydride was obtained in the second distillation, and the yield was 4%. Thus, the total yield was 85%.

Then, 315.1 kg of the total of the first and second distillates (the crude reaction products) was rectified under a pressure of 160 torr at 45° C. In this rectification, refluxing was conducted for 1 hr. After cutting out 6 kg of the initial distillate, the middle distillate was taken out, thereby to obtain 38 kg of a rectified product which is colorless and transparent. By chemical analysis, this rectified product was found to contain up to 0.5 wt % of trifluoromethanesulfonic acid ester, up to 0.5 wt % of trifluoromethanesulfonic acid, up to 5 wt ppm of phosphorus, 40 wt ppm of free fluorine, up to 0.2 wt % of n-$C_9F_{20}$, and at least 99 wt % of trifluoromethanesulfonic acid anhydride. The initial distillate of the rectification, the crude trifluoromethanesulfonic acid anhydride and n-$C_9F_{20}$ of the remaining liquid in the reactor were usable as the fluorine containing solvent.

EXAMPLE 19

At first, a reactor that is the same as that of Example 15 was charged with 240 kg of $(C_3F_7)_3N$ having a purity of at least 99 wt %. Then, 100 kg of trifluoromethanesulfonic acid having a purity of at least 99 wt % was added to the reactor. Then, 75 kg (4.75 moles per 6 moles of trifluoromethanesulfonic acid) of diphosphorus pentoxide was intermittently added to the reactor, in the same manner as that of Example 15, to conduct the reaction. In this reaction, conversion of trifluoromethanesulfonic acid was 93%.

Then, a mixture of $(C_3F_7)_3N$ and trifluoromethanesulfonic acid anhydride was distilled off by simple distillation from the reaction mixture in the same manner as that of Example 18, thereby to obtain 301.2 kg of a first distillate. By chemical analysis, this first distillate was found to contain up to 0.5 wt % of trifluoromethanesulfonic acid ester, up to 0.5 wt % of trifluoromethanesulfonic acid, up to 5 wt ppm of phosphorus, 90 wt ppm of free fluorine, 75.0 wt % of $(C_3F_7)_3N$, and 25.0 wt % of trifluoromethanesulfonic acid anhydride. In this first distillation, 226 kg of $(C_3F_7)_3N$ was recovered, and thus the recovery was 94%. In contrast, 75.2 kg of trifluoromethanesulfonic acid anhydride was obtained in the first distillation, and the yield was 80%.

Then, 275 kg of 100% phosphoric acid was added to the residue of the first distillation. Then, a second distillation (simple distillation) was conducted in the same manner as that of Example 18, thereby to obtain 16.7 kg of a second distillate, By chemical analysis, the second distillate was found to contain up to 0.5 wt % of trifluoromethanesulfonic acid ester, up to 0.5 wt % of trifluoromethanesulfonic acid, up to 5 wt ppm of phosphorus, 90 wt ppm of free fluorine, 71.9 wt % of $(C_3F_7)_3N$, and 28.1 wt % of trifluoromethanesulfonic acid anhydride. In this second distillation, 12 kg of $(C_3F_7)_3N$ was recovered. Thus, the recovery was 5% in the second distillation, and the total recovery was 99%. In contrast, 4.7 kg of trifluoromethanesulfonic acid anhydride was obtained in the second distillation, and the yield was 5%. Thus, the total yield was 85%.

Then, 317.9 kg of the total of the first and second distillates (the crude reaction products) was rectified in the same manner as that of Example 18, thereby to obtain 43 kg of a rectified product which is colorless and transparent. By chemical analysis, this rectified product was found to contain up to 0.5 wt % of trifluoromethanesulfonic acid ester, up to 0.5 wt % of trifluoromethanesulfonic acid, up to 5 wt ppm of phosphorus, 20 wt ppm of free fluorine, up to 0.2 wt % of $(C_3F_7)_3N$, and at least 99 wt % of trifluoromethanesulfonic acid anhydride. The initial distillate of the rectification, the crude trifluoromethanesulfonic acid anhydride and $(C_3F_7)_3N$ of the remaining liquid in the reactor were usable as the fluorine-containing solvent.

EXAMPLE 20

At first, a reactor that is the same as that of Example 13 was charged with 240 kg of $(C_4F_9SO_2)_2O$ which is the same as that of Example 13. Then, 100 kg of $C_4F_9SO_3H$ having a purity of at least 99 wt % was added to the reactor. Then, 75 kg (9.5 moles per 6 moles of $C_4F_9SO_3H$) of diphosphorus pentoxide was intermittently added in parts to the mixture, by the same manner as that of Example 15, to conduct the reaction, while the solvent was maintained at 25° C., by allowing heat medium to flow through the jacket, with stirring. In this reaction, conversion of $C_4F_9SO_3H$ was 95%.

Then, the procedure of the first distillation of Example 13 was repeated, thereby to obtain 310.8 kg of $(C_4F_9SO_2)_2O$ which is colorless and transparent. By chemical analysis, this first distillate was found to have the same purity and the same is impurity concentrations as those of the first distillate of Example 13. The actual amount of $(C_4F_9SO_2)_2O$ produced by the reaction was 70.8 kg, and the yield was 73%, based on the amount of $C_4F_9SO_3H$.

Then, 275 kg of 100% phosphoric acid was added to the residue of the above simple distillation. Then, $(C_4F_9SO_2)_2O$ was again distilled off in the same manner as that of the second distillation of Example 13. With this, there was obtained 5.8 kg of $(C_4F_9SO_2)_2O$ which is colorless and transparent. By chemical analysis, this second distillate was found to have the same purity and the same impurity concentrations as those of the second distillate of Example 13. The yield was 6%, based on the amount of $C_4F_9SO_3H$. Thus, the total yield was 79%.

Separately, 316.6 kg of the obtained crude $(C_4F_9SO_2)_2O$ was rectified in the same manner as that of Example 13, thereby to obtain 200 kg of a rectified product which is colorless and transparent. By chemical analysis, this rectified product was found to have the same purity and the same impurity concentrations as those of Example 13. The initial distillate of the rectification and the crude $(C_4F_9SO_2)_2O$ of the remaining liquid in the reactor were usable as the fluorine containing solvent.

EXAMPLE 21

At first, a reactor that is the same as that of Example 13 was charged with 240 kg of $(C_8F_{17}SO_2)_2O$ that is the same as that of Example 14. Then, 100 kg of $C_5F_{17}SO_3H$ having a purity of at least 99% was added to the reactor. Then, 75 kg (15.9 moles per 6 moles of $C_5F_{17}SO_3H$) of diphosphorus pentoxide was intermittently added in parts to the solution mixture, in the same manner as that of Example 15 except that the reaction temperature was 40° C., to conduct the reaction, while the solvent was maintained at 35° C., by allowing heat medium to flow through the jacket, with stirring. In this reaction, conversion of $C_5F_{17}SO_3H$ was 91%.

Then, $(C_8F_{17}SO_2)_2O$ was distilled off in the same manner as that of Example 14, thereby to obtain 303.8 kg of $(C_8F_{17}SO_2)_2O$ which is colorless and transparent. By chemical analysis, this first distillate was found to have the purity and the same impurity concentrations as those of Example 14. The actual amount of $(C_8F_{17}SO_2)_2O$ produced by the reaction was 63.8 kg, and the yield was 65%, based on the amount of $C_5F_{17}SO_3H$.

Then, 275 kg of 100% phosphoric acid was added to the residue of the above simple distillation. Then, $(C_8F_{17}SO_2)_2O$ was again distilled off in the same manner as that of Example 14. With this, there was obtained 3.9 kg of $(C_8F_{17}SO_2)_2O$ which is colorless and transparent. By chemical analysis, this second distillate was found to have the same purity and the same impurity concentrations as those of Example 14. The yield was 4%, based on the amount of $C_5F_{17}SO_3H$. Thus, the total yield was 69%.

Separately, 307.7 kg of the obtained crude $(C_8F_{17}SO_2)_2O$ was rectified in the same manner as that of Example 14, except that 31 kg of the initial distillate was cut out. In this rectification, there was obtained 198 kg of a rectified product which is colorless and transparent. By chemical analysis, this rectified product was found to have the same purity and the same impurity concentrations as those of Example 14. The initial distillate of the rectification and the crude $(C_8F_{17}SO_2)_2O$ of the remaining liquid in the reactor were usable as the fluorine-containing solvent.

What is claimed is:

1. A method for producing a fluoroalkylsulfonic acid anhydride represented by the formula $(C_nF_{2n+1}SO_2)_2O$ where n is an integer ranging from 1 to 8, the method comprising:
   (a) reacting diphosphorus pentoxide with a fluoroalkylsulfonic acid represented by the formula $C_nF_{2n+1}SO_3H$ where n is an integer ranging from 1 to 8, in a fluorine-containing solvent, thereby to form said fluoroalkylsulfonic acid anhydride in said fluorine-containing solvent.

2. A method according to claim 1, wherein said step (a) comprises:
   (1) adding said diphosphorus pentoxide to said fluorine-containing solvent, thereby to prepare a slurry;
   (2) adding said fluoroalkylsulfonic acid to said slurry, thereby to prepare a reaction mixture; and
   (3) maintaining said reaction mixture at a temperature of from −40° to 150° C., thereby to allow said diphosphorus pentoxide to react with said fluoroalkylsulfonic acid in said fluorine-containing solvent.

3. A method according to claim 1, wherein said fluorine-containing solvent is selected from the group consisting of fluoroalkylsulfonic acid anhydrides represented by the formula $(C_nF_{2n+1}SO_2)_2O$ where n is an integer ranging from 1 to 8, fluoroalkylsulfonic acid esters represented by the formula $C_nF_{2n+1}SO_2OC_nF_{2n+1}$ where n is an integer ranging from 1 to 8, perfluoroalkanes represented by the formula $C_nF_{2n+2}$ where n is an integer ranging from 4 to 20, perfluoroalkylamines represented by the formula $(C_nF_{2n+1})_aN$ where n is an integer ranging from 2 to 6, perfluoro polyethers, and mixtures thereof.

4. A method according to claim 1, wherein, after said step (a), said fluoroalkylsulfonic acid anhydride is recovered by:
   (b) recovering said fluoroalkylsulfonic acid anhydride from a first reaction mixture formed by said step (a), thereby to leave a first residue;
   (c) adding phosphoric acid to said first residue, thereby to prepare a second reaction mixture; and
   (d) further recovering said fluoroalkylsulfonic acid anhydride from said first residue contained in said second reaction mixture, by distillation, thereby to leave a second residue.

5. A method according to claim 4, wherein said step (b) is conducted by one of solvent extraction and distillation.

6. A method according to claim 5, wherein said step (b) is conducted by said distillation.

7. A method according to claim 4, wherein said phosphoric acid of the step (c) is devoid of free water.

8. A method according to claim 1, wherein said diphosphorus pentoxide is in an amount not greater than 80 wt %, based on the total weight of said diphosphorus pentoxide and said fluorine-containing solvent.

9. A method according to claim 2, wherein said diphosphorus pentoxide of said step (1) is in an amount of from 2 to 66.7 moles per 6 moles of said fluoroalkylsulfonic acid of said step (2).

10. A method according to claim 3, wherein said fluorine-containing solvent is a fluoroalkylsulfonic acid anhydride.

11. A method according to claim 4, wherein said phosphoric acid of the step (c) has a $P_2O_5$ concentration of at least 72.4%.

12. A method according to claim 4, wherein said phosphoric acid of the step (c) is in an amount such that the total of said phosphoric acid and said first residue contains up to 2 moles of bound water, per mol of the total, on a basis of $P_2O_5$, of said phosphoric acid and said diphosphorus pentoxide contained in said first residue.

13. A method according to claim 12, wherein said phosphoric acid is in said amount such that said second residue of said step (d) becomes a pyrophosphoric acid solution.

14. A method according to claim 13, wherein an amount of water is added to said pyrophosphoric acid solution such that there is prepared a phosphoric acid solution that is substantially devoid of free water and is usable as said phosphoric acid of said step (c).

15. A method according to claim 4, wherein said step (b) is conducted by filtration under a pressure of at least 50 torr.

16. A method according to claim 2, wherein said step (3) is conducted at a temperature of from 0° to 10° C. for at least 30 minutes under atmospheric pressure or a reduced pressure.

17. A method according to claim 1, wherein said step (a) comprises:
(1') adding said fluoroalkylsulfonic acid to said fluorine-containing solvent, thereby to prepare a solution;
(2') adding said diphosphorus pentoxide to said solution, thereby to prepare a reaction mixture; and
(3') maintaining said reaction mixture at a temperature of from −40° to 150° C., thereby to allow said diphosphorus pentoxide to react with said fluoroalkylsulfonic acid in said fluorine-containing solvent.

18. A method according to claim 17, wherein said diphosphorus pentoxide of said step (2') is in an amount of from 2 to 100 moles per 6 moles of said fluoroalkylsulfonic acid of said step (1').

19. A method according to claim 17, wherein said step (2') is conducted by intermittently adding said diphosphorus pentoxide in parts to said solution, and said step (3') is conducted at a temperature of from 20° to 40° C. for at least 30 minutes under atmospheric pressure or a reduced pressure.

20. A method for producing a fluoroalkylsulfonic acid anhydride comprising:
(a) reacting diphosphorus pentoxide with a fluoroalkylsulfonic acid, thereby to produce said fluoroalkylsulfonic acid anhydride;
(b) recovering said fluoroalkylsulfonic acid anhydride from a first reaction mixture formed by said step (a), thereby to leave a residue;
(c) adding phosphoric acid to said residue, thereby to prepare a second reaction mixture; and
(d) further recovering said fluoroalkylsulfonic acid anhydride from said residue contained in said second reaction mixture, by distillation.

21. A method for producing a trifluoromethanesulfonic acid anhydride comprising:
(a) reacting diphosphorus pentoxide with a trifluoromethanesulfonic acid, in a fluorine-containing solvent, thereby to form said trifluoromethanesulfonic acid anhydride in said fluorine-containing solvent.

22. A method according to claim 21, wherein said step (a) comprises:
(1) adding said diphosphorus pentoxide to said fluorine-containing solvent, thereby to prepare a slurry;
(2) adding said trifluoromethanesulfonic acid to said slurry, thereby to prepare a reaction mixture; and
(3) maintaining said reaction mixture at a temperature of from −40° to 100° C., thereby to allow said diphosphorus pentoxide to react with said trifluoromethanesulfonic acid in said fluorine-containing solvent.

23. A method according to claim 21, wherein said fluorine-containing solvent is selected from the group consisting of trifluoromethanesulfonic acid anhydride, trifluoromethyltrifluoromethanesulfonate represented by the formula $CF_3SO_2OCF_9$, perfluoroalkanes represented by the formula $C_nF_{2n+2}$ where n is an integer ranging from 4 to 20, perfluoroalkylamines each represented by the formula $(C_nF_{2n+1})_3N$ where n is an integer ranging from 2 to 6, perfluoro polyethers, and mixtures thereof.

24. A method according to claim 21, wherein, after said step (a), said trifluoromethanesulfonic acid anhydride is recovered by:
(b) recovering said trifluoromethanesulfonic acid anhydride from a first reaction mixture formed by said step (a), thereby to leave a first residue;
(c) adding phosphoric acid to said first residue, thereby to prepare a second reaction mixture; and
(d) further recovering said trifluoromethanesulfonic acid anhydride from said first residue contained in said second reaction mixture, by distillation, thereby to leave a second residue.

25. A method according to claim 24, wherein said step (b) is conducted by one of solvent extraction and distillation.

26. A method according to claim 25, wherein said step (b) is conducted by said distillation.

27. A method according to claim 24, wherein said phosphoric acid of the step (c) is devoid of free water.

28. A method according to claim 21, wherein said diphosphorus pentoxide is in an amount not greater than 80 wt %, based on a total weight of said diphosphorus pentoxide and said fluorine-containing solvent.

29. A method according to claim 21, wherein said diphosphorus pentoxide is in an amount of from 2 to 20 moles per 6 moles of said trifluoromethanesulfonic acid.

30. A method according to claim 23, wherein said fluorine-containing solvent is said trifluoromethanesulfonic acid anhydride.

31. A method according to claim 24, wherein said phosphoric acid of the step (c) has a $P_2O_5$ concentration of at least 72.4%.

32. A method according to claim 24, wherein said phosphoric acid is in an amount such that the total of said phosphoric acid and said first residue contains up to 2 moles of bound water, per mol of the total, on the basis of $P_2O_5$, of said phosphoric acid and said diphosphorus pentoxide contained in said first residue.

33. A method according to claim 32, wherein said phosphoric acid is in said amount such that said second residue of said step (d) becomes a pyrophosphoric acid solution.

34. A method according to claim 33, wherein an amount of water is added to said pyrophosphoric acid solution such that there is prepared a phosphoric acid solution that is substantially devoid of free water and is usable as said phosphoric acid of said step (c).

35. A method according to claim 24, wherein said step (b) is conducted under a pressure of at least 50 torr.

36. A method according to claim 22, wherein said step (3) is conducted at a temperature of from 0° to 10° C. for at least 30 minutes under atmospheric pressure or a reduced pressure.

37. A method for producing a trifluoromethanesulfonic acid anhydride comprising:
- (a) reacting diphosphorus pentoxide with a trifluoromethanesulfonic acid, thereby to produce said trifluoromethanesulfonic acid anhydride;
- (b) recovering said trifluoromethanesulfonic acid anhydride from a first reaction mixture formed by said step (a), thereby to leave a residue;
- (c) adding phosphoric acid to said residue, thereby to prepare a second reaction mixture; and
- (d) further recovering said trifluoromethanesulfonic acid anhydride from said residue contained in said second reaction mixture, by distillation.

38. A method according to claim 3, wherein said fluorine-containing solvent is a member selected from the group consisting of fluoroalkylsulfonic acid anhydrides, perfluoroalkanes, perfluoroalkylamines, and mixtures thereof.

39. A method according to claim 38, wherein said fluoroalkylsulfonic acid anhydride is $(CF_3SO_2)_2O$ or $(C_4F_9SO_2)_2O$, said perfluoralkane is $n\text{-}C_9F_{20}$, and said perfluoroalkylamine is $(C_3F_7)_3N$.

* * * * *